US008512252B2

(12) United States Patent
Ludomirsky et al.

(10) Patent No.: US 8,512,252 B2
(45) Date of Patent: Aug. 20, 2013

(54) DELIVERY METHOD AND SYSTEM FOR MONITORING CARDIOVASCULAR PRESSURES

(75) Inventors: Achiau Ludomirsky, St. Louis, MO (US); David Goetzinger, Livonia, MI (US); Catherine Morgan, Ann Arbor, MI (US); Nader Najafi, Ann Arbor, MI (US)

(73) Assignee: Integrated Sensing Systems Inc., Ypsilanti, MI (US)

( * ) Notice: Subject to any disclaimer, the term of this patent is extended or adjusted under 35 U.S.C. 154(b) by 2090 days.

(21) Appl. No.: 11/163,840

(22) Filed: Nov. 1, 2005

(65) Prior Publication Data

US 2006/0047205 A1 Mar. 2, 2006

Related U.S. Application Data

(63) Continuation-in-part of application No. 10/679,888, filed on Oct. 6, 2003, now abandoned.

(60) Provisional application No. 60/416,406, filed on Oct. 7, 2002, provisional application No. 60/416,407, filed on Oct. 7, 2002, provisional application No. 60/416,408, filed on Oct. 7, 2002, provisional application No. 60/416,409, filed on Oct. 7, 2002.

(51) Int. Cl.
*A61B 5/02* (2006.01)

(52) U.S. Cl.
USPC .............................. 600/486; 600/483; 600/485

(58) Field of Classification Search
USPC ................. 600/481, 483–486, 488, 500–508, 600/561, 302
See application file for complete search history.

(56) References Cited

U.S. PATENT DOCUMENTS

| 5,368,040 | A | 11/1994 | Carney | 128/700 |
|---|---|---|---|---|
| 6,053,873 | A | 4/2000 | Govari | 600/505 |
| 6,277,078 | B1 | 8/2001 | Porat | 600/486 |
| 6,328,699 | B1 | 12/2001 | Eigler et al. | 600/486 |
| 6,330,885 | B1 * | 12/2001 | Weissman et al. | 128/899 |
| 6,409,674 | B1 * | 6/2002 | Brockway et al. | 600/486 |
| 6,442,413 | B1 | 8/2002 | Silver | |
| 6,636,769 | B2 | 10/2003 | Govari et al. | |
| 6,689,056 | B1 * | 2/2004 | Kilcoyne et al. | 600/300 |
| 6,855,115 | B2 * | 2/2005 | Fonseca et al. | 600/488 |

(Continued)

OTHER PUBLICATIONS

U.S. Appl. No. 10/679,664, filed Oct. 6, 2003, Najafi, et al.

*Primary Examiner* — Navin Natnithithadha
(74) *Attorney, Agent, or Firm* — Hartman Global IP Law; Gary M. Hartman; Domenica N. S. Hartman

(57) ABSTRACT

A delivery method and system for noninvasively monitoring cardiac physiologic parameters used to evaluate patients with cardiovascular conditions. The system includes an implantable sensing device configured for chronic implantation in a cavity of the cardiovascular system, such as the heart, pulmonary artery (PA), etc. The method involves introducing the sensing device through a cardiovascular cavity that is upstream in the vasculature from the cavity where implantation is intended and has a larger diameter than the intended cavity, and thereafter blood flow through the cardiovascular system delivers the device to the intended cavity. The device is sized and configured so as to secure itself within the intended cavity when the device moves through the cavity to a point where the diameter narrows sufficiently to secure the device and so as to be oriented once secured to sense a pressure either within, upstream (wedge), or downstream (distal) of the cavity.

15 Claims, 3 Drawing Sheets

(56) References Cited

U.S. PATENT DOCUMENTS

| | | | |
|---|---|---|---|
| 6,936,003 B2* | 8/2005 | Iddan | 600/114 |
| 7,083,578 B2* | 8/2006 | Lewkowicz et al. | 600/593 |
| 7,147,604 B1 | 12/2006 | Allen et al. | |
| 7,425,200 B2* | 9/2008 | Brockway et al. | 600/486 |
| 7,481,771 B2* | 1/2009 | Fonseca et al. | 600/486 |
| 7,567,692 B2* | 7/2009 | Buzaglo et al. | 382/128 |
| 7,577,283 B2* | 8/2009 | Zinaty et al. | 382/128 |
| 7,647,090 B1* | 1/2010 | Frisch et al. | 600/473 |
| 7,699,059 B2* | 4/2010 | Fonseca et al. | 128/899 |
| 2002/0138009 A1* | 9/2002 | Brockway et al. | 600/485 |
| 2002/0151816 A1* | 10/2002 | Rich et al. | 600/547 |
| 2003/0040685 A1* | 2/2003 | Lewkowicz et al. | 600/593 |
| 2004/0176664 A1* | 9/2004 | Iddan | 600/160 |
| 2005/0065589 A1 | 3/2005 | Schneider et al. | 607/126 |
| 2006/0047205 A1* | 3/2006 | Ludomirsky et al. | 600/486 |
| 2006/0287602 A1* | 12/2006 | O'Brien et al. | 600/486 |

* cited by examiner

DELIVERY METHOD AND SYSTEM FOR MONITORING CARDIOVASCULAR PRESSURES

CROSS REFERENCE TO RELATED APPLICATIONS

This is a continuation-in-part patent application of U.S. patent application Ser. No. 10/679,888, filed Oct. 6, 2003, which claims the benefit of U.S. Provisional Application Nos. 60/416,406, 60/416,407, 60/416,408, and 60/416,409, each of which was filed on Oct. 7, 2002. The contents of these applications are incorporated herein by reference.

BACKGROUND OF THE INVENTION

The present invention generally relates to the field of implantable medical devices for monitoring physiological parameters. More particularly, the invention relates to a system and delivery method for monitoring cardiovascular pressures using an implantable pressure sensor, such as for monitoring the progression and treatment of congestive heart failure, congenital heart disease, pulmonary hypertension, and other conditions of the cardiovascular system.

Various conditions of the cardiovascular system can be diagnosed and monitored by sensing pressures within the heart and coronary arteries. A particularly complex example is a type of congenital heart disease (CHD) in which the heart consists of only one functional ventricle. In order to provide such patients with appropriate solutions, multiple surgical procedures are required to enable the single ventricle to serve as the systemic ventricle, while the lungs receive blood flow via different anastomosis (Fontan Baffle). A key dilemma in the treatment of these patients is the timing of the different surgical stages. The inclination is to perform the surgeries at a younger age. However, if performed too early, the outcome is dismal. Currently, the only way to assess the hemodynamic status is by invasive cardiac catheterization, requiring admission of the patient to a catheterization lab. Pulmonary artery (PA) pressure and resistance are currently used to decide the timing of the different surgical stages.

Another condition diagnosed and monitored by evaluating PA pressure is primary pulmonary hypertension (PPH). In addition to direct invasive measurement using a catheterization procedure, Doppler echocardiography has been used as a method for evaluating pulmonary hypertension, though it too requires specialized equipment in a dedicated laboratory. The course of patients with PPH is usually long and chronic, and many treatment modalities have been proposed but none to date provide an absolute solution. Therefore, following diagnosis of pulmonary hypertension, it would be preferable to noninvasively monitor this condition on a continuing basis in order to optimize treatment.

Congestive heart failure (CHF) is a condition in which a damaged or overworked heart cannot pump adequately to meet the metabolic demands of the body and/or can do so only with an elevated ventricular diastolic pressure. CHF is a major health problem worldwide, affecting millions of patients and accounts for numerous hospitalizations. Overall, the cost of treating CHF is very high (billions of dollars annually) and involves numerous physician visits. From 1979 to 1999, CHF deaths increased 145% and hospital discharges increased 155%. Survival is poor with 20% dying within one year and only 50% of patients surviving more than five years. The many patients suffering from this progressive, fatal disease tend to have an extremely poor quality of life and become increasingly unable to perform routine daily tasks.

Left ventricular (LV) filling pressure is a key factor in the progression of CHF. LV filling pressure represents the diastolic pressure at which the left atrium (LA) and left ventricle (LV) equilibrate, at which time the LV fills with blood from the LA. As the heart ages, cardiac tissue becomes less compliant, causing the LV filling pressure to increase. This means that higher pressures are required from the LA in order to fill the LV. The heart must compensate for this to maintain adequate cardiac output (CO). However, increasing the LA pressure strains the heart and over time irreversible alteration will occur.

Left ventricular end diastolic pressure (LVEDP) and mean left atrium pressure (MLAP) are the primary factors physicians use to evaluate CHF patients. MLAP and LVEDP (plotted in FIG. 1) correspond directly with LV filling pressure and are easy for physicians to identify from LV pressure data. The physician's ultimate goal is to increase cardiac output (CO) while reducing LVEDP. Treatment methods include medications, lifestyle changes, pacemakers, and/or surgery.

As with the above-noted CHD and PPH conditions, the only current method for evaluating intracardiac pressures such as MLAP and LVEDP is an invasive cardiac catheterization procedure. In certain cases, CHF is complicated by mitral stenosis, necessitating significantly more precise and continuous pressure data. Atrial fibrillation can develop as a result of this condition, and the evaluation of such cases is considerably more complex since pressure gradients across the mitral valve must also be measured. Diagnosis of LV failure and mitral stenosis can be obtained by measuring the pulmonary capillary wedge pressure (PCWP), which provides an indirect measurement of MLAP. The current procedure for measuring PCWP is to advance a balloon-tipped multi-lumen (e.g., Swan-Ganz) catheter through the right atrium (RA) and right ventricle (RV) until the distal tip of the catheter is located within a branch of the pulmonary artery. The balloon is then inflated to occlude the pulmonary artery branch, and a pressure transducer distal of the balloon measures the pressure within the pulmonary artery branch, which drops as a result of the occlusion and stabilizes at a pressure level approximately equal to MLAP.

As with the monitoring of pulmonary hypertension, Doppler echocardiography can be used to evaluate CHF complicated by mitral stenosis, though again with the disadvantages of requiring a specialized laboratory, specialized equipment, and the inability to perform continuous measurements.

In view of the above, it can be appreciated that the treatment of cardiovascular diseases such as CHD, CHF, and pulmonary hypertension could be greatly improved through the capability of continuous or at least intermittent monitoring of various pressures and/or flows in the heart and associated vasculature. Porat (U.S. Pat. No. 6,277,078), Eigler et al. (U.S. Pat. No. 6,328,699), and Carney (U.S. Pat. No. 5,368,040) teach different modes of monitoring heart performance using wireless implantable sensors. In every case, however, what is described is a general scheme of monitoring the heart. The existence of a method to construct a sensor with sufficient size, long-term fidelity, stability, telemetry range, and biocompatibility is noticeably absent in each case, being instead simply assumed. Eigler et al. generally discuss a specific device structure but not the baseline and sensitivity drift issues that must be addressed in any long-term implant. Applications for wireless sensors located in a stent (e.g., U.S. Pat. No. 6,053,873 by Govari) have also been taught, although little acknowledgment is made of the difficulty in fabricating a pressure sensor with telemetry means sufficiently small to be incorporated into a stent.

From the foregoing, it can be appreciated that the current clinical methods for evaluating intracardiac pressures, including those associated with CHF, CHD, and pulmonary hypertension, involve catheterization procedures. In addition to requiring admission of the patient to a catheterization lab, such procedures provide only a snapshot of pressure data, carry morbidity and mortality risks, and are expensive. Therefore, for the diagnosis and monitoring of the progression and treatment of cardiovascular conditions such as CHF, CHD, and pulmonary hypertension, it would be preferable to noninvasively monitor these conditions on a continuing basis to more accurately assess the patient's condition and optimize treatment.

BRIEF SUMMARY OF THE INVENTION

The invention comprises a method and system for noninvasively monitoring cardiac physiologic parameters used to evaluate patients with a cardiovascular condition. The system includes an implantable sensing device that is preferably batteryless and wireless, is configured to be chronically implanted in any of several cavities in the cardiovascular system, such as the heart, pulmonary artery (PA), etc.

The method of this invention involves delivering the sensing device to a first cardiovascular cavity of a human patient for sensing at least one pressure within the cardiovascular system. The method entails placing the sensing device in a second cardiovascular cavity having a larger diameter than the first cardiovascular cavity, and thereafter allowing blood flow through the cardiovascular system to deliver the sensing device to the first cardiovascular cavity. According to the method, the sensing device is sized and configured so as to secure itself within the first cardiovascular cavity as the sensing device moves therethrough, and to be oriented once secured to sense a pressure within the first cardiovascular cavity.

A system of this invention generally entails the sensing device sized and configured for securing itself within the first cardiovascular cavity as the sensing device moves therethrough, and a device or apparatus for placing the sensing device in the second cardiovascular cavity so that blood flow through the cardiovascular system delivers the sensing device to the first cardiovascular cavity, after which the size and configuration of the sensing device enable the sensing device to secure itself within the first cardiovascular cavity as the sensing device moves therethrough and orient itself when secured to sense a pressure within the first cardiovascular cavity.

In view of the above, the sensing device of this invention is intentionally sized and configured to be released in the cardiovascular system and travel with blood flow to its intended destination, though it should be understood that the sensing device can also be delivered by such other modes as percutaneously, surgically, or on a stent. In a preferred embodiment of the invention, once in place the sensing device may be wirelessly interrogated with a reader unit that is not within the first cardiovascular cavity, and is preferably outside the patient's body. In this manner, the sensing device is capable of measuring and transmitting, in real time, any of various physiologic parameters including RV, RA, PA, PCWP, and other pressures within the cardiovascular system. The sensing device and its delivery method are particularly well suited for noninvasively monitoring congestive heart failure (CHF), the change in cardiac physiological parameters of persons with congenital heart disease (CHD), and the response of pulmonary artery hypertension (PPH) to different treatments. In particular, the delivery method of this invention is capable of placing the sensing device in, for example, a branch of the pulmonary artery to measure PCWP or PA pressure for the purpose of monitoring the progression and treatment of CHF, PPH, CHD and other diseases affecting the left ventricle, mitral valve, etc.

The delivery method is also capable of placing the sensing device in such locations as the left ventricle or left atrium to measure LVEDP or MLAP for the purpose of monitoring CHF. Delivery to locations that are not blood vessels requires that the sensing device be equipped with means for securing the device locally, as has been described elsewhere including anchoring means and methods taught in commonly-assigned U.S. Published Patent Application No. 2005/0065589, as well as techniques commonly used for commercial medical implants such as stents and atrial septum plugs. Other data useful to a physician and measurable with the invention (in conjunction with appropriate mathematical algorithms) include, but are not limited to, dp/dt (pressure change over time) of the LV pressure, dp/dt of the LA pressure, dp/dt of the RV pressure, RVEDP (right ventricular end diastolic pressure), and mean RA pressure. Each of these may be measured and/or derived from pressures measured in the appropriate heart cavities. For cases of CHF with mitral valve stenosis, a second implant can be placed such that mitral valve gradient can be assessed, for example, with an implant in the left ventricle (to measure LV pressure) and a second implant in the left atrium (to measure LA pressure) or the pulmonary artery (to measure PCWP).

Monitoring cardiovascular system pressures in accordance with the present invention can provide a physician with one or more of the following advantages: earlier intervention in the course of disease; better tailoring of medications or other treatments and therapies to reduce pulmonary hypertension; identification of other complications from treatments or disease progression; faster feedback on the impact of medications and/or pacing changes on heart function; pacemaker parameter tuning; lower overall treatment costs; and decreased frequency and/or severity of hospitalization for pulmonary-hypertension-related conditions through improved outpatient and home care.

Other objects and advantages of this invention will be better appreciated from the following detailed description.

DETAILED DESCRIPTION OF THE INVENTION

Figure 1:
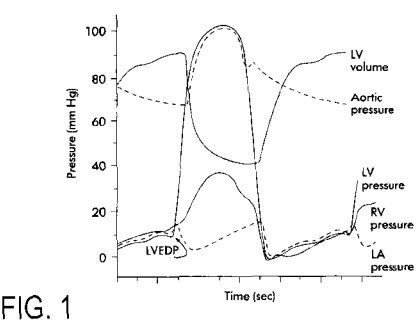
FIG. 1 is a graph of typical waveforms for various pressure points within the heart.
Figure 2:
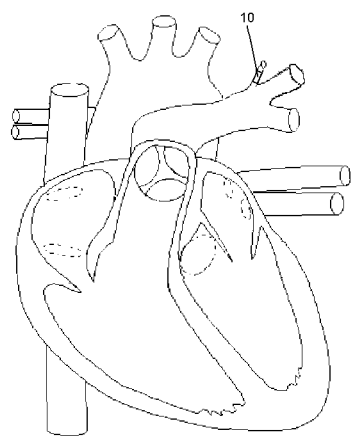
FIG. 2 is a schematic of an implantable pressure monitor anchored in a side artery of the pulmonary artery.

In order to provide for the effective monitoring, management, and tailoring of treatments for conditions of the cardiovascular system, including CHD, CHF, pulmonary hypertension, etc., the present invention provides a sensing system and techniques for delivering an implantable pressure monitor of the system to a location where sensing of a pressure of interest can occur. The implantable pressure monitor is in the form of an implant 10 capable of securely anchoring itself within an artery or vein adjacent the heart, as represented in FIG. 2. The implant 10 may be physically realized with a combination of any of several technologies, including those using microfabrication technology such as Microelectromechanical Systems (MEMS). For example, capacitive and piezoresistive pressure sensors have been fabricated with MEMS technology. The implant 10 may be in the form of a hermetic package of anodically bonded layers of glass and silicon (doped or undoped). A particularly preferred implant 10 is disclosed in commonly-assigned U.S. Pat. No. 6,968,743 to Rich et al., whose contents relating to the design of such an implant are incorporated herein by reference. According to Rich et al, a suitable implant 10 has a biocompatible monolithic structure comprising a transducer integrally microfabricated in a substrate and active circuitry electrically connected to the transducer through conductive paths on the substrate. The exterior of the implant 10 can be defined by an outer shell that houses the microfabricated components of the implant 10, with the transducer being exposed at one end of the implant 10 so as to be exposed to the pressure within the environment of the implant 10.

As will be discussed in further detail below, the implant 10 of this invention is particularly intended to be suitable for placement and sensing PCWP (pulmonary capillary wedge pressure) and PA (pulmonary artery) pressure. According to a preferred aspect of the invention, placement of the implant 10 is accomplished by releasing the implant 10 within the cardiovascular system so that the implant 10 implants itself within a cardiovascular cavity whose cross-sectional diameter is less than that of the implant 10. Notable examples of such cavities include the pulmonary artery, pulmonary veins, and their tributaries.

Figure 3:
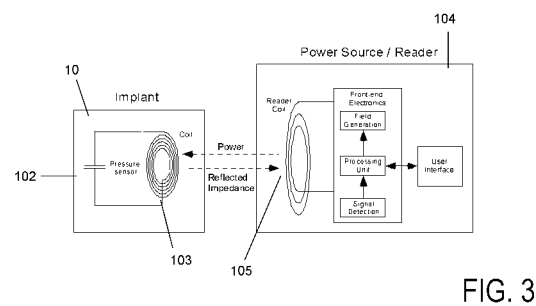
FIG. 3 is a block diagram of a magnetic telemetry based physiologic monitoring system based on a resonant scheme according to a preferred embodiment of the present invention.
Figure 4:
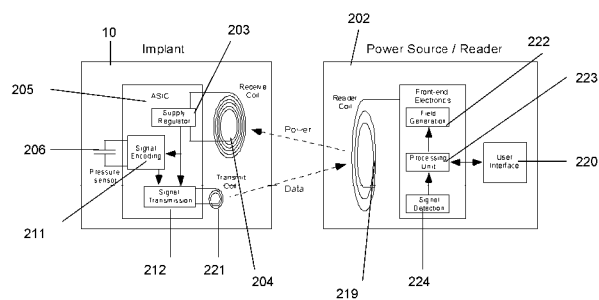
FIG. 4 is a block diagram of a magnetic telemetry based physiologic monitoring system based on a passive scheme according to an alternate embodiment of the present invention.

The implant 10 is preferably used in combination with an external reader unit, examples of which are represented in FIGS. 3 and 4. In the preferred embodiments, the reader unit both transmits power to and receives transmitted data from the implant 10 through a wireless telemetry link. According to a preferred aspect of the invention, in addition to pressure, data transmitted from the implant 10 may include temperature, calibration data, identification data, fluid flow rate, chemical concentration, and/or other physiologic parameters. The reader unit may include a barometric pressure sensor in order to compensate for variation in atmospheric pressure.

The telemetry link between the implant 10 and the reader unit is preferably batteryless, wireless, and implemented using either a resonant or passive, magnetically coupled scheme. A resonant implant 10 (shown in FIG. 3) is the simplest approach, and consists only of a packaged inductor coil 103 and capacitive pressure sensor 102. Together, the sensor 102 and coil 103 form a circuit that has a specific resonant frequency. At that resonant frequency, the circuit presents a measurable change in magnetically coupled impedance load to an external coil 105 associated with an external reader unit 104. Because the resonant frequency is a function of the inductance of the coil 103 and the capacitance of the sensor 102, as pressure changes the resonant frequency changes as well. The external reader unit 104 is able to determine pressure by monitoring the frequency at which the coil antenna 105 impedance changes.

The preferred communication scheme for the present invention, shown in FIG. 4 as being between a passive implant 10 and an external reader unit 202, is based on magnetic telemetry. Devices that have onboard circuitry but still receive their operating power from an external source (i.e., are batteryless) are referred to herein as passive. Without the external reader unit 202 present, the implant 10 lays passive and without any internal means to power itself. When a pressure reading is desired, the reader unit 202 is brought into a suitable range to the implant 10. In this case the external reader unit 202 uses an alternating magnetic field to induce a voltage in the implant 10. When sufficient voltage has been induced in the implant 10, a rectification circuit 203 converts the alternating voltage on the receiver coil 204 into a direct voltage that can be used by electronic circuitry 205 on the implant 10 as a power supply for signal conversion and communication. At this point the implant 10 can be considered alert and, in the preferred embodiment, also ready for commands from the reader unit 202. The maximum achievable communication range is mostly limited by the magnetic field strength necessary to turn the implant 10 on. This telemetry scheme has been proven and used extensively in the identification and tracking industry (e.g., implantable RF ID technology from Texas Instruments or Digital Angel) with a great deal of acceptance and success.

Once the direct voltage in the implant 10 has been established for the circuit operation, a number of techniques may be used to convert the output of the implant 10 into a form suitable for transmission back to the reader unit 202. In the preferred embodiment, a capacitive pressure sensor 206 and sigma delta conversion or capacitance to frequency conversion of the sensor output may be easily used. Capacitive sensors are preferred due to the small power requirements for electronics when reading capacitance values. Many pressure sensors are based on piezoresistive effects and, while suitable for some applications, do suffer in this application due to the higher power levels needed for readout. Sigma delta converters are preferred due to the tolerance of noisy supply voltages and manufacturing variations.

As those skilled in magnetic telemetry are aware, a number of modulation schemes are available for transmitting data via magnetic coupling. The preferred schemes include but are not limited to amplitude modulation, frequency modulation, frequency shift keying, phase shift keying, and also spread spectrum techniques. The preferred modulation scheme may be determined by the specifications of an individual application, and is not intended to be limited under this invention.

In addition to the many available modulation techniques, there are many technologies developed that allow the implant 10 to communicate back to the reader unit 202 the signal containing pressure information. It is understood that the reader unit 202 may transmit either a continuous level of RF power to supply the needed energy for the implant 10, or it may pulse the power allowing temporary storage in a battery or capacitor device (not shown) within the implant 10. Similarly, the implant 10 of FIG. 4 may signal back to the reader unit 202 at any interval in time, delayed or instantaneous, during reader RF (Radio Frequency) transmission or alternately in the absence of reader transmission. The implant 10 may include a single coil antenna 204 for both reception and transmission, or it may include two antennas 204 and 221, one each for transmission and reception, respectively. There are many techniques for construction of the reader coil 219 and processing electronics known to those skilled in the art. In FIG. 4, the reader unit 202 is represented as having front-end electronics that include field generation circuitry 222, signal detection circuitry 224, and a processing unit 223. The reader unit 202 may interface to a display, computer, or other data logging devices 220.

A large number of possible geometries and structures are available for the coil 204 and are known to those skilled in the art. The coil conductor may be wound around a ferrite core to enhance magnetic properties, deposited on a flat rigid or flexible substrate, and formed into a long/skinny or short/wide cylindrical solenoid. The conductor is preferably made at least in part with a metal of high conductivity such as copper, silver, gold. The coil 204 may alternately be fabricated on the same substrate as the pressure sensor 102/206. Methods of fabrication of coils on the sensor substrate include but not limited to one or more or any combination of the following techniques: sputtering, electroplating, lift-off, screen printing, and/or other suitable methods known to those skilled in the art.

The rectification circuitry 203 outputs a constant voltage level for the other electronics from an alternating voltage input. Efficient realizations of such circuitry are standard electronic techniques and may include either full bridge diode rectifiers or half-bridge diode rectifiers in the preferred embodiment. This rectification circuitry may include a capacitor for transient energy storage to reduce the noise ripple on the output supply voltage. This circuitry may be implemented on the same integrated circuit die with other electronics.

As represented in FIG. 4, in addition to the coil antenna 204 and rectification circuitry 203, the electronic circuitry 205 can further include signal conditioning circuitry 211 and signal transmission circuitry 212. The signal conditioning circuit 211 processes an output signal from the sensor 206 and prepares it for transmission to an external receiving and/or analyzing device. For example, many pressure sensors output a capacitance signal that may be digitized for radio frequency (RF) transmission. Accordingly, the signal conditioning circuit 211 places the output signal of the implant 10 into an appropriate form. Many different signal conditioning circuits are known to those skilled in the art. Capacitance to frequency conversion, sigma delta or other analog to digital conversion techniques are all possible conditioning circuits that may be used in a preferred embodiment.

The signal transmission circuitry 212 transmits the encoded signal from the signal conditioning circuitry 211 for reception by the external reader unit 202. Magnetic telemetry is again used for this communication, as the transmission circuitry 212 generates an alternating electromagnetic field that propagates to the reader unit 202. Either the same coil 204 is used for signal reception and for transmission, or alternatively the second coil 221 is dedicated for transmission only.

A third option, particularly useful for (but not limited to) situations in which long-term data acquisition without continuous use of a reader unit is desirable, is to implement the implant 10 using an active scheme. This approach incorporates an additional capacitor, battery, rechargeable battery, or other power-storage element that allows the implant to function without requiring the immediate presence of the reader unit as a power supply. Data may be stored in the implant 10 and downloaded intermittently using the reader unit as required.

In addition to the basic implant-and-reader system, a number of other embodiments of the technology can be realized to achieve additional functionality. The system may be implemented as a remote monitoring configuration, including but not limited to home monitoring, which may include but not limited to telephone based, wireless communication based, or web-based (or other communication means) delivery of information received from the implant by the reader unit to a physician or caregiver.

A closed-loop drug delivery system may also be envisioned. Data from the implant 10 can be fed directly to a drug delivery device (which may or may not be implanted, and may or may not be an integral part of the implant 10). This approach would allow continuous adjustment of medications for pulmonary-hypertension-related conditions with minimal physician intervention.

Implanted sensor data may be used as feedback for a RA-LA unidirectional valve, in either an open-loop or closed-loop configuration, which can be used to treat pulmonary hypertension in at-risk patients. For example, the valve could be modulated to maintain a mean RA-LA pressure of less than 10 mmHg. Pulmonary decompression is accomplished by allowing some blood to flow directly between the RA and LA, thus reducing the PA pressure.

In addition to sensing pressure, the implant 10 can be any suitable miniature sensor adapted to detect and/or monitor various physiological parameters. For example, such a sensor may be a temperature, flow, velocity, impedance, or vibration sensor, or a sensor adapted to measure specific chemistries such as blood or chemical composition, chemical concentration, gas content (e.g., $O_2$ and $CO_2$), and glucose levels. Various specific examples of these types of miniature sensors are known to those skilled in the art, and any one or more of these suitable sensors can be utilized in the implant 10 of the present invention. In addition to sensing physiologic parameters, the described implant 10 could be augmented with various actuation functions. In such case, the implant 10 would be augmented with any of various actuators, including but not limited to: thermal generators; voltage or current sources, probes, or electrodes; drug delivery pumps, valves, or meters; microtools for localized surgical procedures; radiation-emitting sources; defibrillators; muscle stimulators; pacing stimulators, left ventricular assisting device (LVAD). While the specific functionalities of the implant 10 chosen will depend on the application, the size and shape of the implant 10 must be suitable for placement, delivery, and implantation of the implant 10, as discussed below.

The implant may be located in various places within the cardiovascular system, depending on the blood pressure measurement of interest. Because the number of implants 10 is not practically limited by the technology, multiple locations for blood pressure and/or other physiologic parameter measurements are easily established, including all chambers of the heart, major arteries and appendages.

As represented in FIG. 2, the implant 10 is particularly well suited for placement in the pulmonary artery. As depicted in FIG. 2, the implant 10 has a diameter (e.g., less than 5 mm) less than that of the branch of the pulmonary artery in which the implant 10 is intended to be placed, and the implant 10 is released within a larger branch of the pulmonary artery for delivery by blood flow to the desired branch. It will be understood that blood flow will continue to push the implant 10 through any number of pulmonary artery branches with diameters smaller than the diameter of the larger artery used for the injection, until the implant 10 enters a pulmonary artery that is small enough to prevent further progress of the implant 10, at which point the implant 10 becomes wedged or anchored in the pulmonary artery. With this approach, the artery in which the implant 10 has lodged (secured) itself is likely and, for measuring PCWP, preferably occluded, though it should be understood that there are many more pulmonary arteries that will compensate for the blocked artery. As represented in FIG. 2, a suitable exterior shape for the implant 10 to promote a proper orientation of the implant 10 and occlusion of an artery is a cylindrical shape, with the length of the implant 10 preferably being greater than its diameter in order to inhibit migration and pitching (flipping) of the implant 10. While the physical shape and size of the implant 10 can be relied on to secure the implant 10 within the artery, such that the implant 10 does not require a discrete anchoring appendage, cell growth and encapsulation will happen over time, leading to further stabilization of the implant 10. As such, the pressure sensor is positioned in the implant 10 to sense the pressure of interest while there is a layer of cell growth on the implant 10.

Several catheter delivery methods are envisioned for delivering the implant 10 for the purpose of monitoring cardiovascular conditions, including CHF, CHD, PPH, etc., particularly in combination with a remote unit (e.g., the aforementioned reader units 104 and 202) capable of wirelessly communicating and telepowering the implant 10 as described above. In each case, the implant 10 lacks a discrete anchor and no post delivery sutures are used, though it will be appreciated that both anchors and micro-surgical techniques well-known to catheter users, both clinical and research, could be employed for delivery of the implant 10.

According to the invention, a wide variety of catheter styles can be employed, including styles commercially available, commercially available but modified by the user, and custom designs such as those described below and within the capability of one of ordinary skill in the art. Particular catheter styles that can be used include commercially available articulated (or positionable) catheters, standard catheters, and sterilizable tubing (both shrink tubing and non-shrink tubing) used alone or in combination with guidewires and ancillary catheter implements (introducers, sheaths, side ports, Luer lock fluidic ports, etc.) The catheter can be formed of a variety of materials, while its size can be extended to any size used in a relevant clinical procedure, such as between 11 Fr and 14 Fr. In preferred embodiments of the invention, the distal tip of the catheter is modified to temporarily secure the implant 10. For example, the implant 10 can be directly secured to the catheter tip, secured to a length of tubing (shrink or non-shrink) attached (e.g., adhesively or shrink-fit) to catheter tip, or secured by a fixture with lumen affixed to the tip, and then released therefrom using, for example, a hydraulic pulse, tether, ball-style, bearing-style, or collet-style joint, fusible link, Acme magnet, etc. The modification to the catheter tip can provide a variety of functions, including additional degrees of freedom (i.e., rotation at a joint, bending at a joint, etc.). Any modification, fixture, or holder with which the catheter is equipped can be machined, molded, cut from stock, or formed from a wide variety of materials, including but not limited to PEEK™, TEFLON®, polyolefin, PVC shrink tubing, other machinable and formable plastics, metals, etc. Such modifications, fixtures, and holders can be assembled and attached using a wide variety of materials and methods, including but not limited to adhesives, epoxies, solvents, heat, welding, interference fit (friction), hydraulic forces (vacuums), etc. With each approach, the modification of the catheter is intended to allow attachment of the implant 10 to the catheter, provide a means for releasing the implant 10 from the catheter, and provide both control and flexibility of the catheter tip to allow maneuverability through the arteries, veins, and heart.

Suitable catheterization procedures carried out with this invention are similar to standard cardiac and pulmonary artery catheterization procedures that, as will be understood by those familiar with clinical and research catheterization procedures, can involve anywhere from a single insertion to many insertions of various catheter tools, such as sheaths, introducers, guidewires, incision and suturing tools, microsurgery and imaging tools, and so on. During the catheterization procedure, the catheter, its distal tip, and any catheter tools can be tracked with external standard imaging tools such as a fluoroscope. All such equipment is preferably sterilizable by standard clinical and research methods, a preferred example of which is gas mediated sterilization such as but not limited to EtO (ethylene oxide) gas sterilization. It is believed that sterilization soaks could also be used, an example of which is solutions containing glutaric dialdehyde ($C_5H_8O_2$), such as CIDEX®.

Figure 5:
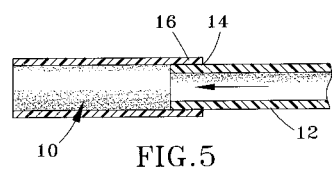
FIGS. 5 through 8 schematically represent a sensor implant and four methods for delivering the implant in accordance with different embodiments of the present invention.

In FIG. 5, a catheter 12 is shown whose distal tip 14 is sized to receive an annular rim 16 formed at one end of an implant 10, and to secure the implant 10 with an adhesive or an interference fit with an annular rim 16 defined by a delivery sleeve. In this embodiment, the rim 16 is pressed over the tip 14 of the catheter 12 where it is held until forcibly displaced from the catheter 12, such as by a hydraulic pulse delivered through the catheter 12 with a suitable fluid, which can be any sterilized fluid commonly used in catheterization and surgical procedures, including but not limited to 0.9% saline, Ringer's solution, and electrolyte replacement solutions.

Figure 6:
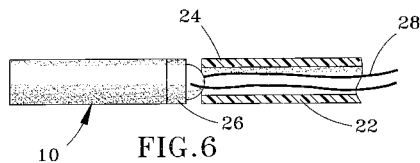

FIG. 6 represents another embodiment in which the implant 10 is configured to have a tether attachment 26 at one end thereof. The catheter 22 is equipped with a tether 28 looped through the attachment 26 to secure the implant 10, with both ends (not shown) of the tether 28 exiting the manipulator (external) portion of the catheter 22 to permit the operator to selectively release the implant 10 from the distal tip 24 of the catheter 22.

Figure 7:
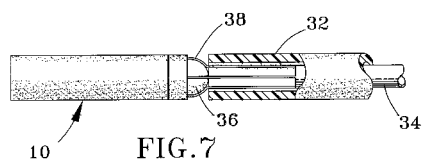

FIG. 7 represents yet another embodiment that employs a collet-style joint for releasably securing the implant 10. The implant 10 formed to have a ball end 36 gripped by multiple spring-loaded collet fingers 38 formed at the end of a collet tube 34 and extending from the distal end of the catheter 32. By retracting the catheter 32 relative to the collet tube 34, the fingers 38 are allowed to resiliently expand and release the implant 10. By gripping the implant 10 in the manner shown, rotation of the collet tube 34 and its fingers 38 allows for angular movement of the implant 10 relative to the catheter 32.

Figure 8:
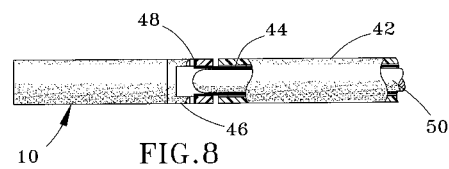

FIG. 8 represents an embodiment similar to that of FIG. 7, but with a catheter 42 provided with a tube 44 equipped with latch fingers 48 that extend from the distal end of the catheter 42, and a lock catheter 50 within the tube 44 that forces the latch fingers 48 radially outward into engagement with catches 46 disposed at one end of the implant 10. By retracting the lock catheter 50, the fingers 48 are allowed to collapse and release the implant 10.

A corollary to the operation of releasing the implant 10 is its recovery. Recovery of the implant 10 is also application dependent, where the degree of tissue growth around the implant 10 may affect the ability to use catheter-based microsurgical tools needed to effect recovery. In addition to long term recovery, there is a need in certain applications for short term or acute recovery (as in, for example during the procedure, should repositioning of the implant 10 be indicated). For recovery, any catheter tool with a physical gripper end, either commercially available or custom made, could be potentially employed. Moreover, the implant 10 itself can be modified to include a handle to allow reattachment to, for example, a mechanical latch, ball joint, tether loop, collet, or any of other designs based on the concept of a feature handle and a means of attaching a tether or modified catheter or catheter tool in-vivo.

The ability of an implant 10 as described above to implant itself in a restricted cavity of the cardiovascular system was demonstrated with a female canine. The procedure involved a pair of implants, both having diameters of about 3.7 mm and with different lengths of either 14.5 or 17.5 mm. Each implant was a completely self-contained unit similar to the implant 10 represented in FIG. 4, and therefore equipped for wirelessly communicating and telepowering with a reader unit (similar to the aforementioned reader unit 202) and equipped with a capacitive pressure sensor disposed at one end of the implant for capacitively sensing pressures to which the exterior of the implant is exposed. Both implants were delivered to a large pulmonary artery with modified positionable catheters (14 Fr), which worked well though some articulation was lost due to mechanical stresses during insertion that interfered with the ability to precisely place the implants at the intended delivery sites. The shorter implant was placed for sensing wedge pressure (PCWP), while the longer implant was intended for proximal PA measurements.

Aside from the modified articulated catheters, the process of insertion used standard catheterization techniques. Following sterilization of all components, each implant was individually loaded in a PEEK™ fixture adhered to the distal end of the catheter, generally similar to the embodiment of FIG. 5. Each fixture held its implant with friction assisted by hydraulic back pressure using a saline solution that was also used to flush the catheter and eject the implants. The saline solution was dispensed with a syringe connected to a three-way Luer lock stopcock. A surgical insertion was made through the groin and each catheter was threaded up through the femoral vein, through the heart, and to the pulmonary artery main branch. At that point, the intention was to place the implants as close as possible to the best target tributary artery as determined by the surgeon on examination of the arterial bed under the fluoroscope. The shorter implant was released with a hydraulic pulse of the saline solution, and thereafter traveled several millimeters with the blood flow from the end of the pulmonary artery main branch and into a side artery with the transducer facing away from the catheter so as to be oriented for sensing PCWP. The longer implant was released in the same manner but unintentionally early, and as a result was delivered to the same site as the shorter implant. The longer implant was oriented for sensing pulmonary artery (PA), i.e., with its backside (opposite the transducer surface) touching the backside of the shorter implant.

Following the catheterization procedure, the implants were detected by placing the antenna of the reader unit along the left side of the spine near the heart. Though the values of the sensed pressures were off scale (about 700 to 900 Torr absolute), suggesting other factors were influencing the transducers of the implants beyond the expected wedge/proximal PA pressures, the procedure nonetheless demonstrated the ability to deliver an implant to a branch of the pulmonary artery for the purpose of sensing PCWP and PA pressures. The implants were noted as being oriented parallel to the spine, with the result that the range of the implant signals was limited because the antenna of the reader unit could not be placed perpendicular to the ferrite coils of the implants. Nonetheless, data signals were detected and recorded for both of the implants.

The initial impression of tissue response was positive, as no evidence of necrosis or infection was seen. One of the implants had a small amount of fibrous growth on the transducer end while the other exhibited almost no growth. The slight buildup of tissue did not appear to interfere with the operation of the implant.

While described above in reference to self-implantation of the implant 10 in a restricted cavity of the cardiovascular system, it will be understood that the implant 10 could be adapted for placement in other cardiovascular cavities. A notable example is the atrial septum, since an implant in the atrial septum would not significantly impede blood flow and would thus minimize the thrombogenic effect of flow turbulence. For such applications, the implant 10 of this invention requires an anchor such as types known and employed with devices already used for implantation, as well as improved anchoring techniques as taught in the aforementioned U.S. Published Patent Application No. 2005/0065589. Devices such as septal occluders, pacemaker leads, left atrial appendage occluders, etc., may be used as carriers for the implant 10. Devices have been made and approved by the FDA to occlude atrial septum defects (a septal occluder) and other vascular holes. As an example, the implant 10 could be equipped with an umbrella structure that can be folded within a catheter for delivery and then expanded for implantation. An important aspect of this approach is that the majority of the implant 10 is preferably located in the right side of the heart, with minimum protrusion in the left side of the heart to reduce the thrombogenicity. To further limit the risk of thrombogenesis, preferred implants 10 of this invention are shaped and sized to have limited protrusion of volume into the blood stream. For example, the implant 10 can be formed to have a preformed or overmolded outer shell formed with existing plastic injection technologies suitable for medical implantation. An outer shell coating can be applied to provide a particularly non-thrombogenic exterior. Suitable coating materials include silicone, hydrogels, parylene, polymer, nitrides, oxides, nitric-oxide generating materials, carbides, silicides, titanium, and combinations thereof.

Pacemaker leads have a well-established history for implantation methods, and similar techniques are possible for use with the implant 10 of this invention. For example, an anchoring appendage such as a screw or barb could be used to attach the implant 10 to a heart or vessel wall. Such an anchor may be molded into a shell that defines the exterior of the implant 10, and screwed into the ventricle wall so that the screw is buried below the wall surface. In addition, the implant 10 may include a mesh to promote tissue growth and anchoring. Another option is to attach the implant 10 with a metal tine or barb placed with a catheter. Such an approach is known to work well in trabeculated areas of the heart, and has therefore been used for implanting pacing leads in the right ventricle. Clips or expanding probes may also be used, both of which would penetrate the heart or vessel wall slightly.

The foregoing disclosure includes the best mode devised by the inventors for practicing the invention. It is apparent, however, that several variations in the apparatuses and methods of the present invention may be conceivable by one skilled in the art. Because the foregoing disclosure is intended to enable one skilled in the pertinent art to practice the instant invention, it should not be construed to be limited thereby, but should be construed to include such aforementioned variations. Therefore, the scope of the invention is to be limited only by the following claims.

What is claimed is:

1. A method of delivering an implantable sensing device to a first cardiovascular cavity of a human patient for sensing at least one pressure within the cardiovascular system of the patient for assessing a cardiovascular condition of the patient, the method comprising the steps of placing the sensing device in a second cardiovascular cavity having a larger diameter than the first cardiovascular cavity, and thereafter releasing the sensing device within the second cardiovascular cavity, delivering the sensing device to the first cardiovascular cavity by pushing the sensing device with blood flowing from the second cardiovascular cavity to the first cardiovascular cavity, and operating the sensing device to sense a pressure within the first cardiovascular cavity, wherein the sensing device is sized and configured so as to secure itself within the first cardiovascular cavity as the sensing device moves therethrough, and so as to be oriented once secured to sense the pressure within the first cardiovascular cavity, wherein the first cardiovascular cavity is a first pulmonary artery and the second cardiovascular cavity is a second pulmonary artery, and wherein the sensing device occludes the first pulmonary artery and is oriented within the first pulmonary artery for measuring pulmonary capillary wedge pressure.

2. The method according to claim 1, wherein the sensing device secures itself to the first cardiovascular cavity as a result of the first cardiovascular cavity having a diameter smaller than the sensing device.

3. The method according to claim 1, further comprising the step of placing the sensing device using a catheter delivery technique.

4. The method according to claim 3 wherein the catheter delivery technique comprises temporarily securing the sensing device at a distal tip of a catheter with an interference fit therebetween.

5. The method according to claim 4, wherein the catheter delivery technique comprises releasing the sensing device from the distal tip of the catheter with hydraulic pressure delivered by the catheter to the sensing device.

6. The method according to claim 3, wherein the catheter delivery technique comprises temporarily securing and subsequently releasing the sensing device at a distal tip of a catheter with a tether.

7. The method according to claim 3, wherein the catheter delivery technique comprises temporarily securing and subsequently releasing the sensing device at a distal tip of a catheter with resilient fingers of a collet within the catheter.

8. The method according to claim 7, wherein the resilient fingers of the collet are expanded to release the sensing device.

9. The method according to claim 7, wherein the resilient fingers of the collet are collapsed to release the sensing device.

10. The method according to claim 1, further comprising the steps of cell growth and encapsulation of the sensing device to stabilize the sensing device in the first cardiovascular cavity.

11. The method according to claim 1, wherein the method is performed for diagnosis or monitoring of the cardiovascular condition of the patient.

12. The method according to claim 11, wherein the cardiovascular condition is pulmonary hypertension.

13. The method according to claim 11, wherein the cardiovascular condition is congenital heart disease.

14. The method according to claim 11, wherein the cardiovascular condition is chronic heart failure.

15. The method according to claim 1, wherein the method is part of at least one procedure chosen from the group consisting of early diagnosis of the cardiovascular condition, early intervention in treatment of the cardiovascular condition, remote monitoring of the patient, tailoring of medications, disease management, identification of complications from the cardiovascular condition, treatment of complications from the cardiovascular condition, feedback regarding the impact of medication on the heart, tuning of pacemaker parameters, feedback regarding the impact of pacing changes on heart function, reduction in frequency and severity of hospitalizations due to the cardiovascular condition, identification of mitral valve stenosis, and treatment of mitral valve stenosis.

* * * * *